US00PP33410P2

(12) United States Plant Patent
Norman

(10) Patent No.: US PP33,410 P2
(45) Date of Patent: Aug. 31, 2021

(54) ***SEQUOIA* TREE NAMED 'GREEN GIGANTOR'**

(50) Latin Name: *Sequoia sempervirens*
Varietal Denomination: Green Gigantor

(71) Applicant: Theodore P. Norman, San Gabriel, CA (US)

(72) Inventor: Theodore P. Norman, San Gabriel, CA (US)

( * ) Notice: Subject to any disclaimer, the term of this patent is extended or adjusted under 35 U.S.C. 154(b) by 0 days.

(21) Appl. No.: 17/017,787

(22) Filed: Sep. 11, 2020

(51) Int. Cl.
*A01H 7/00* (2006.01)

(52) U.S. Cl.
USPC ..... Plt./213

(58) Field of Classification Search
USPC ..... Plt./213
CPC ... A01H 7/00; A01H 5/04; A01H 5/00; A01H 5/12; A01H 5/02
See application file for complete search history.

*Primary Examiner* — June Hwu
(74) *Attorney, Agent, or Firm* — Samuel R. McCoy, Jr.

(57) ABSTRACT

A new and distinct *Sequoia sempervirens* tree named 'Green Gigantor' which is characterized by a freely-branching and densely-foliaged growth habit, a conical tree crown profile, distinct dark green foliage, improved tolerance to atmospheric pollution and improved disease resistance. The claimed plant propagates successfully by softwood stem cuttings and has proven to be uniform and stable in the resulting generations.

3 Drawing Sheets

Latin name of the genus and species: The Latin name of the genus and species of the novel variety disclosed herein is *Sequoia sempervirens*.

Variety denomination: The inventive variety of *Sequoia sempervirens* disclosed herein has been given the variety denomination 'Green Gigantor'.

BACKGROUND OF THE INVENTION

Parentage: The claimed plant is the product of a chance discovery which was found growing in a cultivated area of a commercial nursery in Pasadena, Calif. The claimed plant originated from nursery stock of unnamed *Sequoia sempervirens* plants. The true parentage of the claimed plant is unknown. In 1969, the claimed plant was first noted for its robustness in an urban landscape with improved tolerance to atmospheric pollution when compared to other *Sequoia sempervirens* plants that typify the species. The tree was isolated and further grown on in order to confirm the distinctness and stability of the characteristics initially observed. Upon further evaluation and confirmation of the desirable traits, the claimed tree was finally selected for commercialization and given the variety denomination, 'Green Gigantor'.

Asexual Reproduction: In November of 2019, 'Green Gigantor' was first asexually reproduced in Linden, Calif. by way of softwood stem cuttings and has since further been asexually propagated by way of grafting. The claimed tree was found to asexually reproduce in uniform and stable manner and two successive cycle of vegetative propagation have proven to be true to type.

SUMMARY OF THE INVENTION

The following characteristics have been repeatedly observed and represent the distinguishing characteristics of the new *Sequoia sempervirens* tree, 'Green Gigantor'. These traits, in combination, distinguish 'Green Gigantor' as a new and distinct cultivar.

1. 'Green Gigantor' exhibits an upright ascending, freely-branching and densely-foliaged growth habit with a conical tree crown; and
2. 'Green Gigantor' exhibits foliage with a distinctive dark green color; and
3. 'Green Gigantor' exhibits improved vigor and robustness against atmospheric pollution associated with urban landscapes; and
4. 'Green Gigantor' exhibits improved resistance to Botrytis blight, needle blight and redwood canker.

BOTANICAL DESCRIPTION OF THE PLANT

Figure 1:
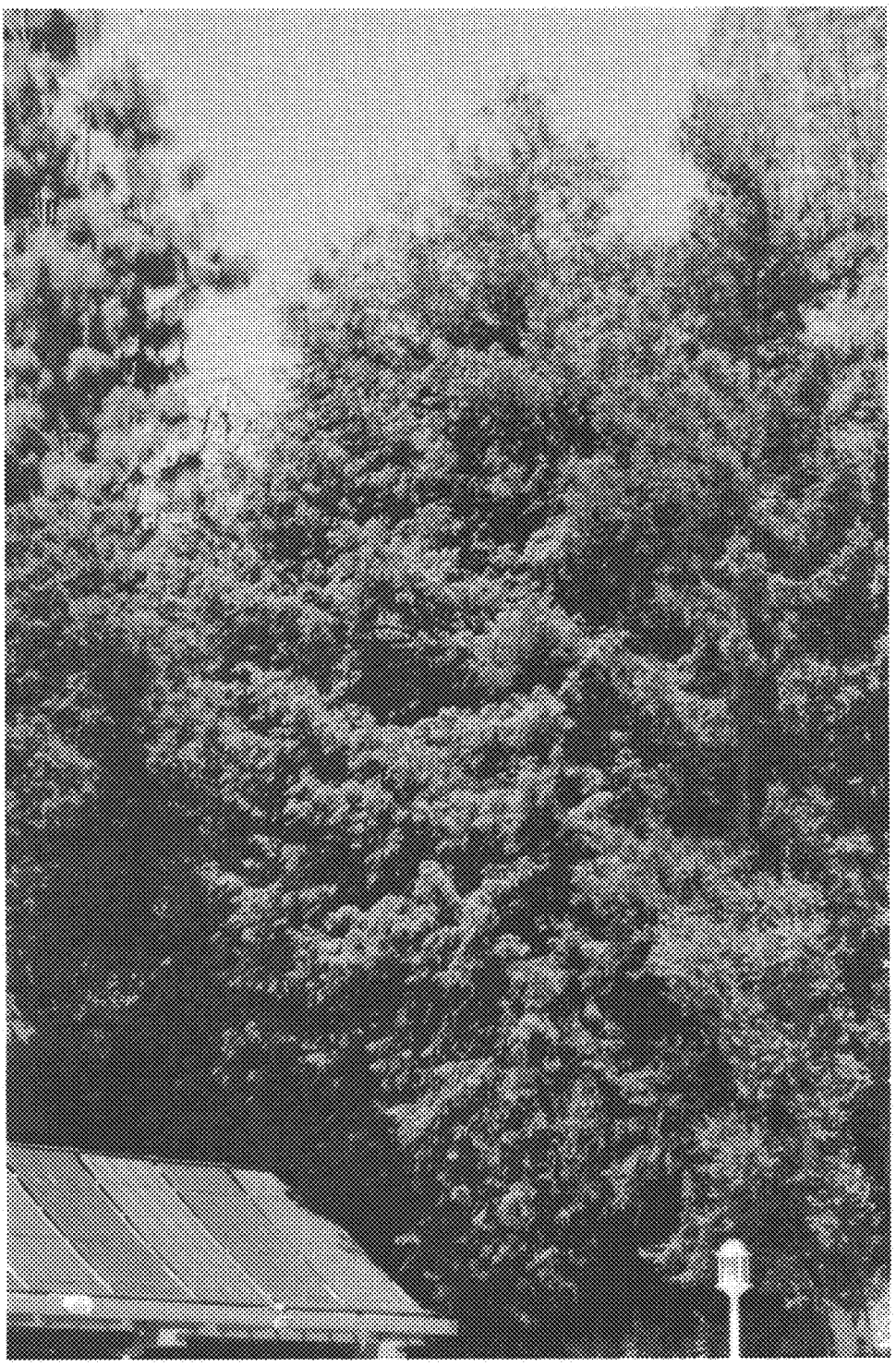
FIG. 1 illustrates, as nearly true as it is reasonably possible to make the same in color photographs of this type, the original 'Green Gigantor' tree at approximately 51 years of age, being grown in Pasadena, Calif.
Figure 2:
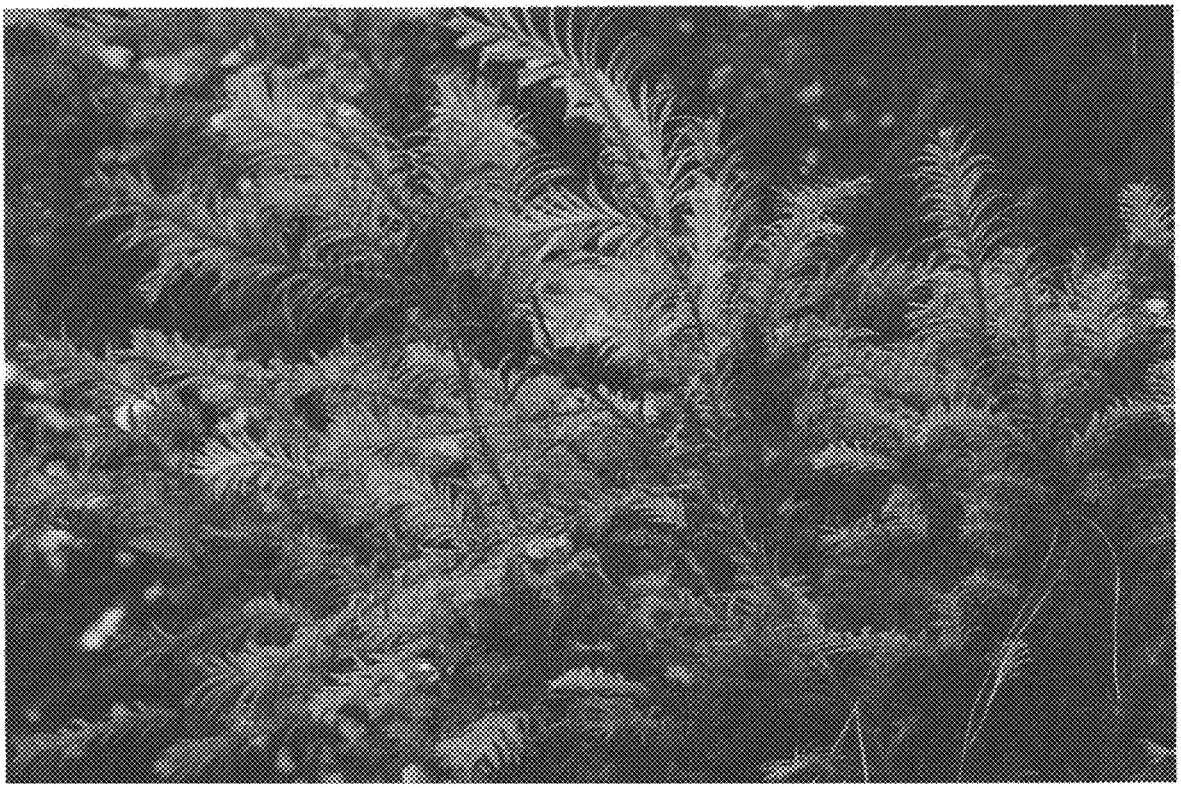
FIG. 2 illustrates, as nearly true as it is reasonably possible to make the same in color photographs of this type, the foliage of 'Green Gigantor'.
Figure 3:
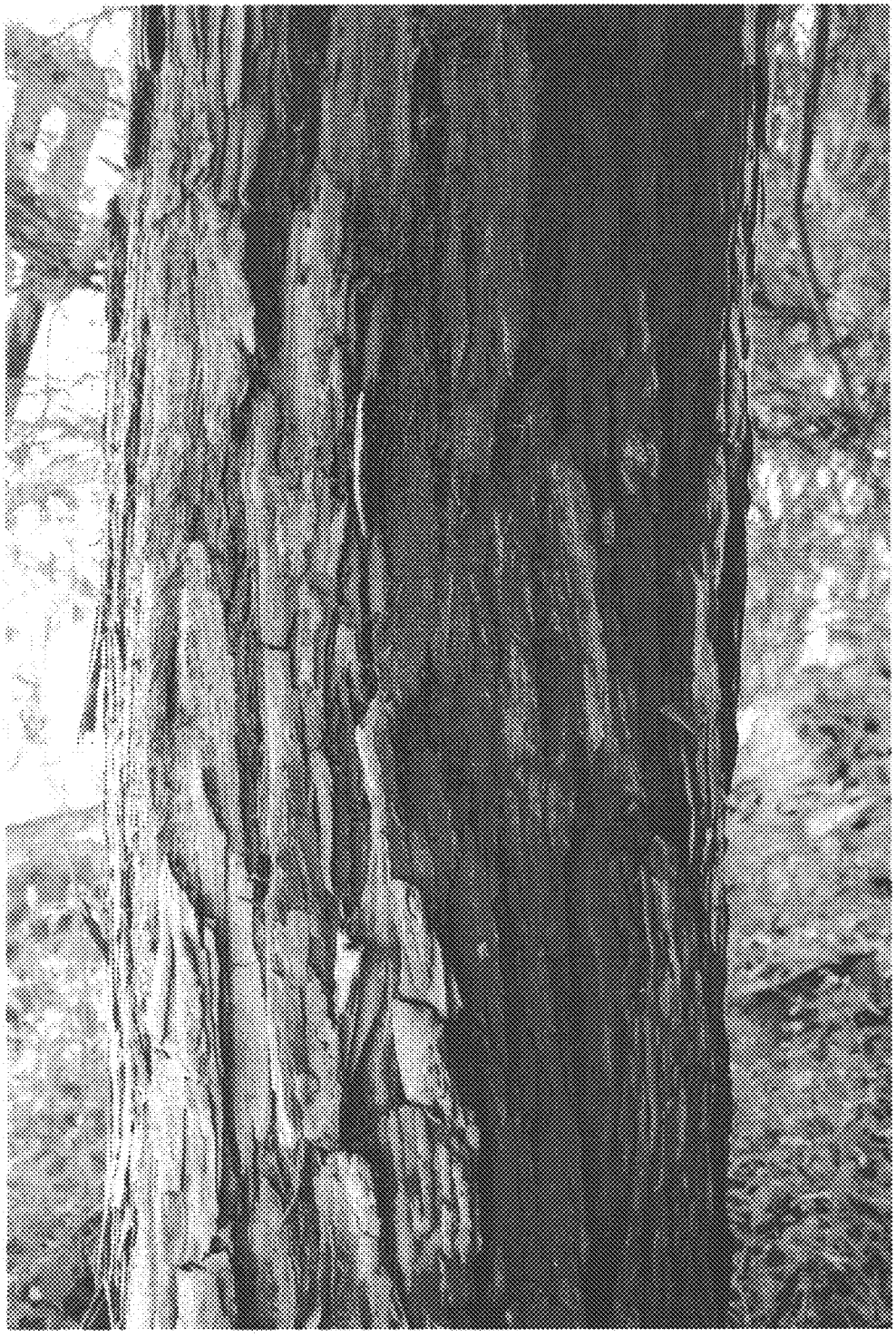
FIG. 3 illustrates, as nearly true as it is reasonably possible to make the same in color photographs of this type, the bark on the oldest wood of 'Green Gigantor'.

The following is a detailed botanical description of a new and distinct *Sequoia sempervirens* plant cultivar known as 'Green Gigantor'. Plant observations were made on a 51 year-old mature tree growing in Pasadena, Calif. The observed tree was grown in full exposure to natural sunlight, maintained without the use of supplemental fertilizer or irrigation. No pest or pathogen countermeasures employed. Observation data was recorded in July of 2020.

Those skilled in the art will appreciate that certain characteristics will vary with older or, conversely, younger plants. 'Green Gigantor' has not been observed under all possible environmental conditions. Where dimensions, sizes, colors and other characteristics are given, it is to be understood that such characteristics are approximations or averages set forth as accurately as practicable. The phenotype of the variety may vary with variations in the environment such as season, temperature, light intensity, day length, cultural conditions and the like. Color notations are based on *The Royal Horticultural Society Colour Chart*, The Royal Horticultural Society, London, 1986 edition except where common terms of color are used.

A botanical description of 'Green Gigantor' and comparisons with the presumed parent and most similar commercial cultivar are provided below.

General plant description:

*Plant habit*.—Monoecious evergreen tree with an upright ascending, freely branching growth habit.

*Tree crown profile*.—Conical.

*Dimensions*.—The original tree is now approximately 23 meters tall and 4 meters wide.

*Environmental tolerances*.—Hardy in US Hardiness Zones 7 through 9; prefers moist, loamy soils and filtered to full sun exposure; moderately drought tolerant.

*Pest and disease susceptibility or resistance*.—The claimed tree has consistently exhibited improved resistance to pathogens common to *Sequoia sempervirens*, including Botrytis blight (*Botrytis cinerea*), needle blight (*Cercospora sequoiae*), and redwood canker (*Botryosphaeria dothidea*). The claimed tree has not been observed to be any more or less susceptible or resistant to insect pests common to *Sequoia sempervirens*.

*Propagation*.—Propagation is accomplished using softwood stem cuttings and grafting.

*Crop time*.—Approximately two growing seasons are needed to produce a 45 to 60 cm tall fully rooted cutting ready for transplant into larger nursery containers or directly into the ground for field production.

Root system:

*Description*.—A relatively shallow network of fibrous, non-fleshy roots. Freely branching and dense.

Stems:

*Branching habit*.—A dominant, near-vertical central main stem, occasionally branched, gives rise to an abundance of lateral branches, themselves freely branching in a single plane, and terminating with small branchlets also born in the same plane. Main stem; central leader — Quantity — One; occasionally branching. Attitude — Erect; near vertical. Aspect — Generally rounded. Diameter — 157 cm, at the base of the trunk. Texture — Becoming progressively fissured with age; oldest wood is strongly fissured; fibrous. Color — Outermost wood is faded to a mixture greyed-white and greyed-green, nearest to RHS 156D and 196C, and irregularly flecked and blotched with greyed-green, RHS 197D. Inner wood in fissures is greyed-orange, nearest to a mixture of RHS 166C and 166D. Strength — Very strong. Lateral branches — Branch angle to main axis — Near 90 degrees. Attitude — Branches drooping with age. Aspect — Circular to terete. Diameter — 30 cm at the base of oldest lateral branches. Texture, juvenile — Smooth, glabrous; stomata sparsely covering juvenile branches. Texture, mature — Lightly to moderately fissured; fibrous. Color, juvenile — Yellow-green, nearest to RHS 147A. Color, mature — Outermost wood is nearest to a mixture greyed-white and greyed-green, RHS 156B and RHS 197D. Inner wood is greyed-orange, nearest to in between RHS 166C and 166D. Stem strength — Strong. Branchlets — Branchlet angle to main axis — Typically ranging from 30 to 45 degrees. Aspect — Circular; somewhat angular. Diameter — 3.1 mm at the base. Color — Yellow-green, nearest to RHS 147A. Texture — Smooth, glabrous; stomata sparsely covering branchlets. Luster — Glossy. Stem strength — Moderately strong.

Foliage:

*Arrangement*.—Alternate to spiraled.

*Attachment*.—Sessile.

*Division*.—Simple.

*Shape*.—Linear to narrowly elliptic.

*Attitude*.—Typically at an acute angle to the branch; occasionally adpressed on the juvenile lateral branches.

*Length*.—40 to 50 mm.

*Width*.—4.0 to 5.0 mm.

*Apex*.—Acute to acuminate.

*Base*.—Broadly acute to obtuse.

*Margin*.—Entire.

*Aspect*.—Flat; occasionally with a slight longitudinal twist; moderately recurved.

*Texture and pubescence, adaxial surface*.—Lightly glandular and glossy.

*Texture and pubescence, abaxial surface*.—Densely glandular and matte.

*Color*.—Juvenile foliage, adaxial surface — Yellow-green, nearest to in between RHS 144B and 144C. Juvenile foliage, abaxial surface — Yellow-green, nearest to in between RHS 144C and 144D. Mature foliage, adaxial surface — Yellow-green, nearest to RHS 147A. Mature foliage, abaxial surface — Yellow-green, nearest to RHS 147A, on the midrib and margins, with the balance of the surface heavily suffused with white, RHS 157A, due to the presence of stomatal bands.

*Venation*.—Pattern — Parallel. Vein color, adaxial surface — Yellow-green, nearest to RHS 147A. Vein color, abaxial surface — Midrib is yellow-green, nearest to RHS 147A; no other visible venation.

*Stipules*.—Absent.

Inflorescence: To date, no flowering has been observed on the mother plant or any progeny therefrom.

Flower bud: To date, no flowering has been observed on the mother plant or any progeny therefrom.

Flower: To date, no flowering has been observed on the mother plant or any progeny therefrom.

Reproductive organs: To date, no flowering has been observed on the mother plant or any progeny therefrom.

Fruit and seed: To date, no fruiting has been observed on the mother plant or any progeny therefrom.

Comparison With the Presumed Parent Plant

Plants of the new cultivar 'Green Gigantor' differ from the parent, an unnamed *Sequoia sempervirens* tree (not patented), by the characteristics described in Table 1. The pollen parent is presumed to also be an unnamed *Sequoia sempervirens* tree (not patented), and therefore no additional comparison to the pollen parent is disclosed.

TABLE 1

| Characteristic | 'Green Gigantor' | The parent |
|---|---|---|
| Resistance to atmospheric pollution. | More resistant. | Less resistant. |
| Disease resistance. | More resistant. | Less resistant. |
| General coloration of the foliage. | Darker shade of green. | Lighter shade of green. |

Comparison With the Most Similar *Sequoia sempervirens* Cultivar Known to the Inventor Plants of the new cultivar 'Green Gigantor' are most similar to the commercial cultivar, *Sequoia sempervirens* 'Aptos Blue' (not patented). A comparison of 'Green Gigantor' with *Sequoia sempervirens* 'Aptos Blue' is described in Table 2.

TABLE 2

| Characteristic | 'Green Gigantor' | 'Aptos Blue' |
|---|---|---|
| Resistance to atmospheric pollution. | More resistant. | Less resistant. |
| Disease resistance. | More resistant. | Less resistant. |
| General coloration of the foliage. | Dark green. | Blue-green. |

That which is claimed is:

1. A new and distinct variety of *Sequoia sempervirens* tree named 'Green Gigantor', substantially as described and illustrated herein.

* * * * *